(12) United States Patent
Wetzl et al.

(10) Patent No.: US 11,455,734 B2
(45) Date of Patent: Sep. 27, 2022

(54) METHOD AND DEVICE FOR AUTOMATIC MOTION DETECTION IN MEDICAL IMAGE-SERIES

(71) Applicant: Siemens Healthcare GmbH, Erlangen (DE)

(72) Inventors: Jens Wetzl, Spardorf (DE); Seung Su Yoon, Erlangen (DE); Christoph Forman, Erlangen (DE); Michaela Schmidt, Uttenreuth (DE); Elisabeth Hoppe, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 149 days.

(21) Appl. No.: 16/851,380

(22) Filed: Apr. 17, 2020

(65) Prior Publication Data
US 2020/0334829 A1    Oct. 22, 2020

(30) Foreign Application Priority Data
Apr. 17, 2019  (EP) ..................................... 19169805

(51) Int. Cl.
*G06K 9/00* (2022.01)
*G06T 7/20* (2017.01)
*G06T 7/149* (2017.01)
*G06T 7/70* (2017.01)
*A61B 5/00* (2006.01)
(Continued)

(52) U.S. Cl.
CPC .............. *G06T 7/20* (2013.01); *A61B 5/0044* (2013.01); *A61B 5/055* (2013.01); *G01R 33/5601* (2013.01); *G01R 33/56509* (2013.01); *G06N 3/0454* (2013.01); *G06N 3/08* (2013.01); *G06T 7/149* (2017.01); *G06T 7/70* (2017.01); *G06T 2207/10088* (2013.01); *G06T 2207/20081* (2013.01); *G06T 2207/20084* (2013.01); *G06T 2207/30048* (2013.01)

(58) Field of Classification Search
CPC ..................................................... G06T 11/003
See application file for complete search history.

(56) References Cited

U.S. PATENT DOCUMENTS

2010/0240996 A1* 9/2010 Ionasec .................. G06T 7/262
                                                        600/443
2014/0376795 A1* 12/2014 Lamash ................ G06T 3/4053
                                                        382/131
(Continued)

OTHER PUBLICATIONS

Kingma et al., "Adam: A Method for Stochastic Optimization," 3rd International Conference for Learning Representations (ICLR), San Diego, 2015, arXiv:1412.6980.
(Continued)

*Primary Examiner* — Hadi Akhavannik
(74) *Attorney, Agent, or Firm* — Banner & Witcoff Ltd.

(57) ABSTRACT

In a method for automatic motion detection in medical image-series, a dataset of a series of images is provided. The images can be of a similar region of interest that are recorded at consecutive points of time. The method can further include localizing a target in the images of the dataset and calculating a position of the target in the images to calculate localization data of the target, and calculating movement data of a movement of the target of temporal adjacent images of the images based on the localization data.

20 Claims, 5 Drawing Sheets

(51) Int. Cl.
- A61B 5/055 (2006.01)
- G01R 33/56 (2006.01)
- G01R 33/565 (2006.01)
- G06N 3/04 (2006.01)
- G06N 3/08 (2006.01)

(56) References Cited

U.S. PATENT DOCUMENTS

| | | | | |
|---|---|---|---|---|
| 2016/0163042 | A1* | 6/2016 | Wollenweber | G06T 11/003 382/131 |
| 2018/0165808 | A1* | 6/2018 | Bagci | A61B 6/037 |
| 2018/0240235 | A1* | 8/2018 | Mazo | G06T 7/0012 |
| 2018/0293762 | A1* | 10/2018 | Fu | G06T 11/003 |

OTHER PUBLICATIONS

Johnson et al., "Three Dimensional, Time Resolved Motion of the Coronary Arteries," Journal of cardiovascular magnetic resonance; vol. 6; No. 3; 2004; pp. 663-673; XP055623015; US; ISSN: 1097-6647; DOI: 10.1081/JCMR-120038086; 2004.

Chefd'Hotel et al., "Flows of Diffeomorphisms for Multimodal Image Registration," IEEE International Symposium on Biomedical Imaging, 2002, pp. 753-756.

Maekelae, et al., "A review of cardiac image registration methods," IEEE Transactions on Medical Imaging; vol. 21; No. 9; Sep. 2002; pp. 1011-1021; XP055519139; US; ISSN: 0278-0062; DOI: 10.1109/TMI.2002.804441; 2002.

Piccini et al., "Automated Cardiac Resting Phase Detection in 2D cine MR images for Acquisition Window Selection in High-Resolution Coronary MRI," Prod. Intl. Soc. Mag. Reson. Med., 2017, vol. 25, pp. 2862, indexsmart.mirasmart.com/ISMRM2017/PDFfiles/2862.html.

Robbins et al., "A stochastic approximation method," Springer, 1985, pp. 400-407.

Bizopoulos et al., "Deep Learning in Cardiology," arxiv.org; Cornell University Library, 201 Olin Library Cornell University Ithaca; NY; Feb. 22, 2019; pp. 1-27; XP081034876; DOI: 10.1109/RBME.2018.2885714; 2019.

Jandt et al., "Automatic generation of time resolved 4D motion vector fields of coronary arteries," Proceeding of the International meeting on fully three-dimensional image reconstruction in radiology and nuclear medicine; Jul. 9, 2007; pp. 249-252; XP002518076; 2007.

Bernard Al., "Deep Learning Techniques for Automatic MRI Cardiac Multi-Structures Segmentation and Diagnosis: Is the Problem Solved?," IEEE Transactions on Medical Imaging; IEEE Service Center; Piscataway, NJ, US; vol. 37; No. 11; Nov. 2018; pp. 2514-2525; XP011693853; ISSN: 0278-0062; DOI: 10.1109/TMI.2018.2837502; 2018.

Ronneberger et al., "U-Net: Convolutional Networks for Biomedical Image Segmentation," Medical Image Computing and Computer-Assisted Intervention (MICCAI), Springer, LNCS, vol. 9351, pp. 234-241, 2015 //arXiv: 1505.04597 [cs.CV].

Yoon et al., "Automatic Cardiac Resting Phase Detection for Static Cardiac Imaging Using Deep Neural Networks," 2018, https://submissions.mirasmart.com/ISMRM2019/ViewSubmissionPublic.aspx?sei=DSyblGRci.

European Search Report dated Sep. 25, 2019, Application No. 19169805.9.

* cited by examiner

METHOD AND DEVICE FOR AUTOMATIC MOTION DETECTION IN MEDICAL IMAGE-SERIES

CROSS REFERENCE TO RELATED APPLICATIONS

This patent application claims priority to European Patent Application No. 19169805.9, filed Apr. 17, 2019, which is incorporated herein by reference in its entirety.

BACKGROUND

Field

The disclosure describes a method and a device for automatic motion detection in medical image-series, especially for controlling a medical imaging system, e.g. a magnetic resonance imaging system, depending on the motion of a target.

Related Art

In medical imaging, there is often the need to reduce the influence of movements of objects in order to record images with minimum movement artefacts, especially in the case where the recording process requires a significant recording time like in magnetic resonance imaging (MRI). For example, in case of obtaining static cardiac imaging such as whole-heart coronary imaging by Cardiovascular Magnetic Resonance (CMR), the operator has to determine a quiescent window within the cardiac cycle, the "resting phase" in which acquisition can be performed without (or with as little as possible) cardiac motion. This quiescent window could either be the end-systolic or end-diastolic resting phase (RP).

Regarding MRI, the detection of resting phases is usually based on a CINE image series and has to be performed accurately by manual inspection, e.g. by a four chamber-view (4CHV) and requires user experience. A normal heartbeat has typically two resting phases in the end-systolic and end-diastolic phases of the cardiac cycle, where the movement of the heart is lowest. In the case of faster heart rates or arrhythmia, one of both of these resting phases can be shortened to the point where image acquisition becomes infeasible.

While electrocardiography (ECG) is commonly used to synchronize CMR measurements to the cardiac cycle, a direct detection of the resting phases from the ECG curve is currently infeasible. To overcome this imperfection, the determination of resting phases is currently commonly done by the MR operator by the acquisition and manual inspection of time-resolved CMR imaging (CINE imaging).

Afterwards, the resting phase parameters are transferred to the acquisition protocol of the static imaging sequence. It is desirable to automatize the workflow of manual detection as it needs user experience and is time-consuming: to make static cardiac imaging faster and more robust.

A further complicating factor for the detection of resting phases is that different cardiac anatomies rest at different times of the cardiac cycle, e.g. the end-systolic resting phase of the atria is earlier than that of the ventricles. A human operator may not necessarily determine a resting phase targeted specifically to the anatomy of interest. An automated approach for determining region-specific resting phases could improve the results and provide targeted scans in the three-dimensional static cardiac images. Consequently, to obtain the resting phases for several regions would give improvements with respect to achieving high quality and precise results. Conversely, if whole-heart coverage is needed, the intersecting set of all region-specific resting phases would give the optimal acquisition window within minimal motion in all regions.

This problem appears not only in MRI during CMR, but in connection with all medical imaging systems recording moving targets (objects or organs), at least in the case the recording time is significant in respect to the movement of the recorded target.

In clinical practice, the current workflow of detection of the resting phase of an organ or object is still performed by a medical expert through visual inspection of time-resolved imaging. This means the medical expert has to check frame-to-frame where the minimal motion of the organ or object is located. It can be time-consuming and thus expensive, as well as being prone to error.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to improve the known systems, devices and methods to facilitate an improvement in automatic motion detection in medical image-series, especially for controlling a medical imaging system, e.g. a magnetic resonance imaging system, preferably during CMR. A further object of the disclosure is to provide an automatic motion detection in medical image-series, such as cardiac medical image-series. Particularly, an object of the disclosure is to provide an automatic cardiac resting phase detection for static cardiac imaging, especially using deep neural networks.

A method according to the disclosure is suitable for automatic motion detection in medical image-series, especially for controlling a medical imaging system. It should be noted that although a magnetic resonance imaging system (MRI-system) is a preferred system of application, the disclosure is suitable for the motion detection in image series recorded with various medical imaging systems (or for controlling various medical imaging systems), such as fluoroscopy systems, ultrasound systems or computed tomography systems (CT-systems). The method comprises the following steps:

Providing a dataset of a series of images, wherein images of a similar (e.g. the same) region of interest are recorded at consecutive points of time. The dataset comprises digital data of a number of images (also often referred to as "frames" or "time frames") of the same target in a region of interest (ROI), e.g. an organ or an object. The regions of interest of different images may be the same or may differ slightly, this does not matter as long as the target is visible in the individual images.

The images are recorded at discrete points of time that are following each other after certain (preferably regular) time periods and have especially all the same (or at least similar) spatial and temporal resolution. This is preferably achieved with an additionally preprocessing step, where (especially all) images are interpolated to a fixed spatial and temporal resolution to be resolution-independent.

In an exemplary embodiment, the images are recorded during one cycle of a periodic movement of the target, e.g. during a heart cycle. The number of images should be three or bigger, e.g. a minimum of 10 images. The more images are used for the method, the better is the detection of the movement.

Calculating localization data of a target (e.g. an organ or an object) by localizing the target in the images of the dataset and calculating the position of this target in these images. This could be performed with a localizer described more accurately in the following.

Calculating movement data of the movement of the target on the basis of temporal adjacent images based on the localization data. This could be performed with a motion detector described more accurately in the following. However, the steps of calculating localization data and calculating the movement data could also be performed in one combined step as also described more accurately in the following.

The method could be implemented by first calculating the localization data of a target (by a localizer) then sending the localization data to a motion detector and then calculating the movement data of the object on the basis of temporal adjacent images with the motion detector based on the localization data. However, with a suited system, the calculation of the localization data and movement data could also be performed in a convoluted manner.

The advantage of the method according to the disclosure is that it achieves an accurate and efficient automatic detection of the resting phases for several targets or regions (e.g. of a heart) with high image quality and without the need for manual user interaction. This could be used for the purpose of performing subsequent static imaging (e.g. 3D imaging). It should be noted that the disclosure does not need to include the entire field-of-view. it only needs to localize targets to provide the detection of localized resting phases. Thus, the motions or other objects outside of the target do not influence the result. Thus, any kind of artifacts in regions of the image that do not contribute to the movement reduction are not affecting the result.

A system for automatic motion detection in medical image-series, preferably for controlling a medical imaging system comprises the following components:

A data interface designed for receiving a dataset of a series of images of a similar region of interest recorded at consecutive points of time. This data interface may be designed for communicating with an RIS (Radiology Information System) a PACS (Picture Archiving and Communication System) or another data-network, e.g. a LAN, WLAN or the internet.

A localizer designed for calculating localization data of a target by localizing the target in the images of the dataset and calculating the position of this target in these images. This localizer may comprise a computer or may be a process in a computer. Thus, the localizer is used for spatial localization of the desired target in a region of interest. It is configured to detect the target as a virtual object and calculate the position of this object relative to a predefined coordinate system or relative to other objects in the images. The localization data may be the calculated coordinates or other (preferably additional) information about the position (or e.g. size) of the target.

A motion detector designed for calculating movement data of the movement of the target on the basis of temporal adjacent images based on the localization data. This motion detector may comprise a computer or may be a process in a computer. Thus, the motion detector is used for derivation of the temporal motion information. In an exemplary embodiment, the same network is used for all ROIs, not specific to any anatomy. In an easy example where the localization data are simply coordinates of a moving target, the motion detector may be designed for calculating the movement data on the basis of the localization data (coordinates) of the target in temporal adjacent images. However, regarding the movement of the heart, the calculations are typically more advanced in praxis as described in the following.

A controller according to the disclosure for controlling a medical imaging system, e.g. a magnetic resonance imaging system comprises a system according to the disclosure. Alternatively or additionally it is configured to perform the method according to the disclosure.

The controller may comprise additional units or devices for controlling components of a medical imaging system, regarding the example of a magnetic resonance imaging system, it could comprise e.g. a sequence controller for measurement sequence control, a memory, a radio-frequency transmitter that generates, amplifies and transmits RF pulses, a gradient system interface, a radio-frequency receiver to acquire magnetic resonance signals and/or a reconstructor to reconstruct magnetic resonance image data.

A medical imaging system, preferably a magnetic resonance imaging system, a fluoroscopy system, an ultrasound system or a computed tomography system, comprises a controller according to the disclosure.

Some units or modules of the system or the controller mentioned above can be completely or partially realized as software modules running on a processor of a system or a controller. A realization largely in the form of software modules can have the advantage that applications already installed on an existing system can be updated, with relatively little effort, to install and run these units of the present application. The object of the disclosure is also achieved by a computer program product with a computer program that is directly loadable into the memory of a device of a system or a controller of a magnetic resonance imaging system, and which comprises program units to perform the steps of the inventive method when the program is executed by the controller or the system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor of a controller or a system. A processor can comprise one or more microprocessors or their equivalents.

In a method according to an exemplary embodiment, the localization data are calculated by performing calculations based on probabilistic boosting trees and/or random forests or based on an adaptive algorithm trained for localizing a target in the images of the dataset and calculating the position of this target in these images. A target may be identified by its individual contour or shape in the images. An adaptive algorithm could be trained on a plurality of test images with labelled targets.

In a method according to an exemplary embodiment, the movement data (of the target) is calculated based on image registration of a target in temporal adjacent images. In an exemplary embodiment, this is achieved by registration of the target of one image in a small region around the center point of the target in the temporal adjacent image.

In an exemplary embodiment, the movement data (of the target) is calculated based on an adaptive algorithm trained for calculating movement data on the basis of temporal adjacent images based on the localization data. Such adaptive algorithm could be trained on a plurality of test images with targets, wherein the localization data of the targets are given and the movement of the target is known.

In an exemplary embodiment, the calculation of the movement data (of the target) and the calculation of the localization data is performed in a convoluted manner with the same adaptive algorithm. Such adaptive algorithm could be trained on a plurality of test images with labeled targets, wherein the localization data of the targets are given and the movement of the target is known. It could be very advantageous to label the shape of a target in the images as indicator for certain movement states.

In a method according to an exemplary embodiment, in the course of calculating the movement data (of the target), a quantitative motion curve is generated describing the average motion magnitude between temporal adjacent images. In an exemplary embodiment, an elastic image registration on the series of images, preferably combined with averaging lengths of motion vectors between temporal adjacent images, is performed in this course. Alternatively, an adaptive algorithm is trained with elastic image registration on the series of images, preferably combined with averaging the length of motion vectors between temporal adjacent images. Since the use of such a trained algorithm is faster than the elastic image registration, the elastic registration (preferably followed by averaging of the motion vector lengths), should serve as a ground truth for the training of the algorithm. The algorithm itself should directly learn to predict the averaged value directly instead of performing the calculation steps of a registration followed by averaging.

In praxis this could be achieved as follows. A ground truth for the motion detection algorithm (e.g. a neural network) is computed based on elastic registration between adjacent image time points, i.e. calculating where pixels that belong to the target structure will move from one time point to the next. If the average of this movement is low, this is considered a resting phase. Based on this ground truth, the algorithm is trained to predict this average movement value. So in such method steps no elastic registration is performed, but the trained algorithm provides results characterizing the motion of the target.

According to a method according to an exemplary embodiment, a motion detection is performed by comparing the calculated movement data (of the target) with a predefined threshold movement value. This could be done in the course of the calculation of the motion or in an additional step. In an exemplary embodiment, this threshold movement value is obtained from some predefined annotated example cases and/or chosen based on physiological knowledge. Alternatively or additionally, the threshold could be chosen depending on a predefined image resolution, e.g. for a resolution of 1 mm a structure (the position of a target or parts of its shape) may not move more than 0.5 mm.

According to a method according to an exemplary embodiment, before calculating the movement data (of the target), the localization data is used for cropping (especially rectangular) areas as a bounding box from the images of the dataset containing the target. In case of segmentation, in an exemplary embodiment, the tightest fitting (especially rectangular) bounding box enclosing the contours of all time-points of the target (segmented region) is selected.

A method according to an exemplary embodiment includes an automatic motion detection in CINE data, wherein a target of the images comprises image data of the coronary arteries (RCA, LAD, LCX) and/or the right or left atrium (RA/LA) and/or the right or left ventricle (RV/LV).

Depending on the application, two or more objects may be localized in the images, wherein two or more landmarks and/or contours are obtained. The motion data is then preferably calculated based on the relative movement between two or more objects. However, better results are achieved if not only relative distances are taken into account, but at least one global coordinate of one target. Thus, it is preferred to track at least one target "globally". It is particularly preferred that a target is chosen for this "global tracking" that is in a consistent motion state, wherein the relative motions to other structures should be the same. Then it is possible to depict all examined structures without motion artifacts.

In a system according to an exemplary embodiment, the localizer comprises a landmark detector configured to obtain landmark position data and/or a center point based on the position of the target, wherein the landmark detector preferably comprises a 3D-DenseNet. In the case, the landmark detection is accomplished with an adaptive algorithm, the landmark detector could also be designated as "landmark detection network".

Alternatively or additionally, the localizer comprises a segmentor configured to obtain contours around a target or a segmented region, wherein the segmentor preferably comprises a U-net structure. In the case, the segmentation is accomplished with an adaptive algorithm, the segmentor could also be designated as "segmentation network".

In an exemplary embodiment, the decision, whether segmentation or landmark detection should be performed, is made specific to each anatomy.

According to an exemplary embodiment, the localizer and/or the motion detector comprise a trained machine learning network, especially a deep learning network. This machine learning network is preferably a neural network and/or a convolutional network and/or an end-to-end network. In an exemplary embodiment, the localizer and/or the motion detector are two chained (especially deep) neural networks.

In a system according to an exemplary embodiment, components of the system are part of a data-network, where the data network and a medical imaging system (i.e. the medical imaging system which provides image data) are in data-communication with each other, wherein the data-network preferably comprises parts of the internet and/or a cloud-based computing system, where the system according to the disclosure or a number of components of this system is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved by means of data interfaces and/or data transmission protocols.

In the context of "cloud computing", in an exemplary embodiment of the method, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

In an exemplary embodiment, the abovementioned units (e.g. the localizer, especially a segmentor and/or a landmark detector, or the motion detector) are present on the "cloud" side. A preferred system further comprises, a local computer connected to the system via a data channel (e.g. a data-network, particularly configured as RIS or PACS). The local computer includes at least one data receiving interface to receive data. Moreover, it is preferred if the local computer additionally has a transmission interface in order to send data to the system.

Figure 1:
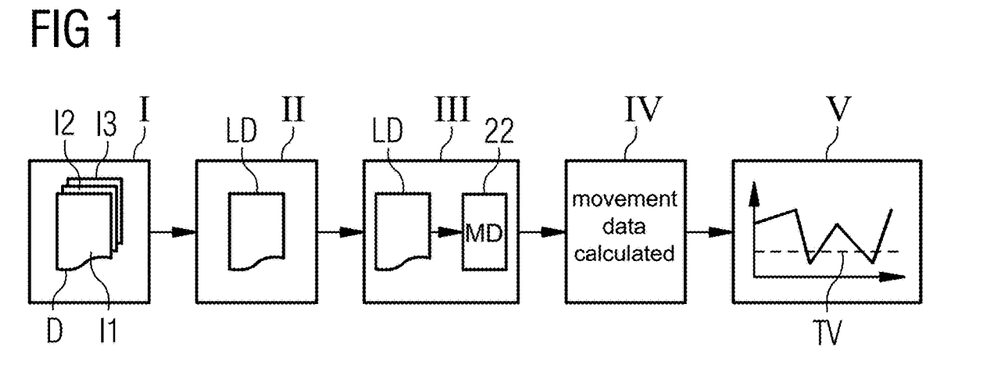
FIG. 1 shows a block diagram of the process flow of a method according to an exemplary embodiment of the disclosure.

FIG. 1 shows a block diagram of the process flow of a method according to an exemplary embodiment of the disclosure for automatic motion detection in medical image-series.

Figure 2:
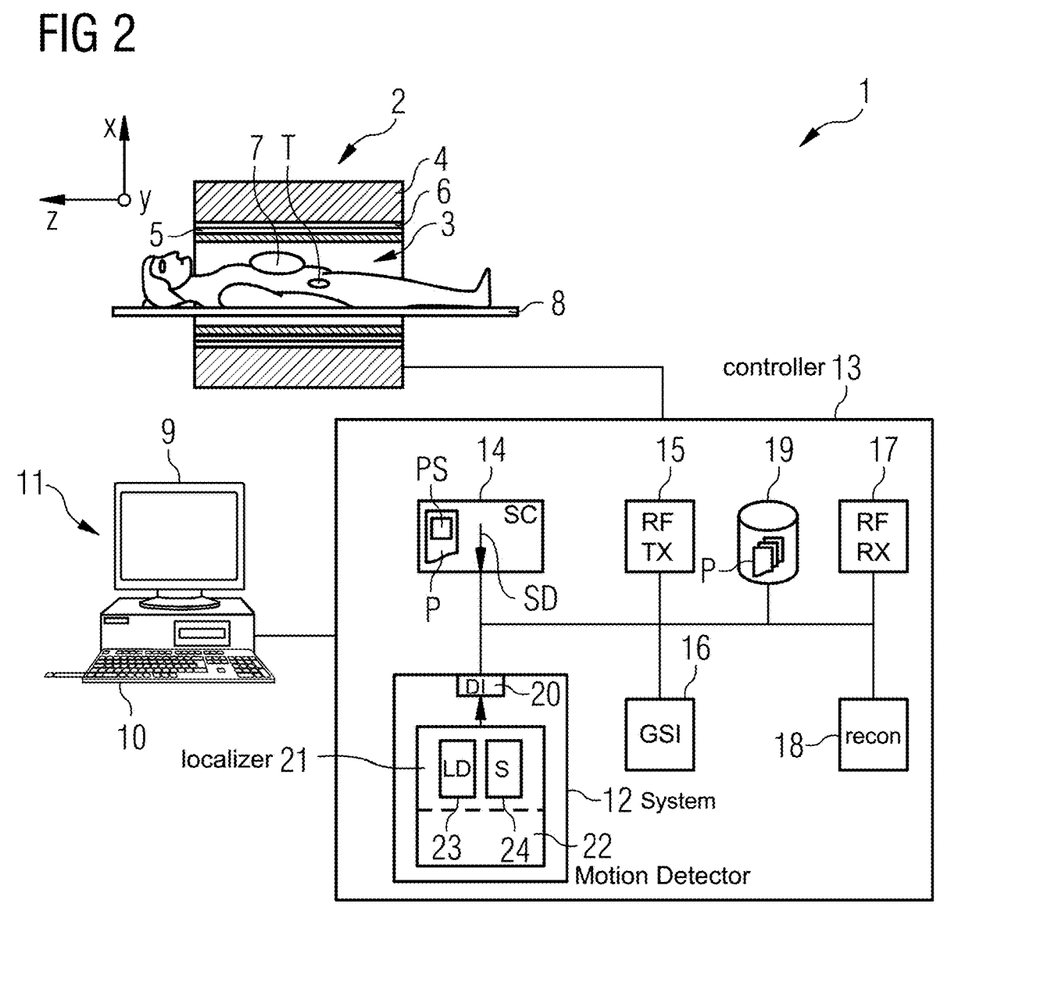
FIG. 2 shows a MRI system according to an exemplary embodiment of the disclosure.

In step I, a dataset D of a series of (medical) images I1, I2, I3 is provided, wherein images I1, I2, I3 of a similar region of interest, where a target T (s. FIG. 2) is localized, are recorded at consecutive points of time.

In step II, localization data LD of a target is calculated by a localizer 21 (s. e.g. FIG. 2) localizing the target T in the images I1, I2, I3 of the dataset D and calculating the position of this target T in these images I1, I2, I3.

In step III, the calculated localization data LD are sent to a motion detector 22 (see also FIG. 2).

In step IV, the movement data of the target T is calculated by the motion detector 22 on the basis of temporal adjacent images I1, I2, I3 based on the localization data LD.

In step V, a motion detection is performed by comparing the calculated movement data of the target T with a predefined threshold movement value TV, wherein this threshold movement value TV is preferably obtained from some predefined annotated example cases or chosen based on physiological knowledge or chosen depending on a predefined image resolution.

FIG. 2 shows a schematic representation of a magnetic resonance imaging system 1 ("MRI-system") as an example for a medical imaging system 1. The MRI system 1 includes the actual magnetic resonance scanner (data acquisition unit) 2 with an examination space 3 or patient tunnel in which a patient or test person is positioned on a driven bed 8, in whose body the actual target T is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed such that a series of images can be recorded during consecutive points of time. It here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central controller 13 that is used to control the MRI system 1. This central controller 13 includes a sequence controller 14 for measurement sequence control. With this sequence controller 14, the series of radio-frequency pulses (RF pulses) and gradient pulses can be controlled depending on a selected pulse sequence PS. For example, such a series of pulse sequence PS can be predetermined within a measurement or control protocol P. Different control protocols P for different measurements or measurement sessions are typically stored in a memory 19 and can be selected by and operator (and possibly modified as necessary) and then be used to implement the measurement.

To output the individual RF pulses of an pulse sequence PS, the central controller 13 has a radio-frequency transmitter 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmitter 15 and the gradient system interface 16 to emit the pulse sequence PS.

Moreover, the controller 13 has a radio-frequency receiver 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the pulse sequence PS.

A reconstructor 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central controller 13 can take place via a terminal 10 with an input and a display 9, via which the entire MRI system 1 can thus also be operated by an operator. MR images can also be displayed at the display 9, and measurements can be planned and started by means of the input (possibly in combination with the display 9), and in particular suitable control protocols can be selected (and possibly modified) with suitable series of pulse sequence PS as explained above.

The controller 13 comprises a system 12 configured to perform the method according to the disclosure. This system 12 comprises the following components that may appear to be software modules.

A data interface 20 configured to receive a dataset D of a series of images I1, I2, I3, wherein images I1, I2, I3 of a similar region of interest are recorded at consecutive points of time (see also FIG. 1).

A localizer 21 designed for calculating localization data LD of a target T by localizing the target T in the images I1, I2, I3 of the dataset D and calculating the position of this target T in these images I1, I2, I3.

A motion detector 22 designed for calculating the movement data of the target T on the basis of temporal adjacent images based on the localization data LD.

In an exemplary aspect, a processor of the controller 13 may execute the computer instructions of the software modules of the system 12 to perform the functions and/or operations of the system 12, including the method according to one or more aspects. In an exemplary embodiment, the system 12 (including one or more components therein) includes processor circuitry that is configured to perform one or more functions and/or operations of the system 12.

The dashed line between the localizer 21 and the motion detector 22 should indicate that these two units could be separate units, wherein the calculated localization data LD are sent to the motion detector 22, or alternatively that these two units could also be combined so that the results are calculated in an interlaced manner.

In this example, the localizer 21 additionally comprises a landmark detector 23 configured to obtain landmark position data or a center point based on the position of the target T and a segmentor 24 configured to obtain contours around a target T or a segmented region.

The MRI system 1 according to the disclosure, and in particular the controller 13, can have a number of additional components that are not shown in detail but are typically present at such systems, for example a network interface in order to connect the entire system with a data-network N and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 3:
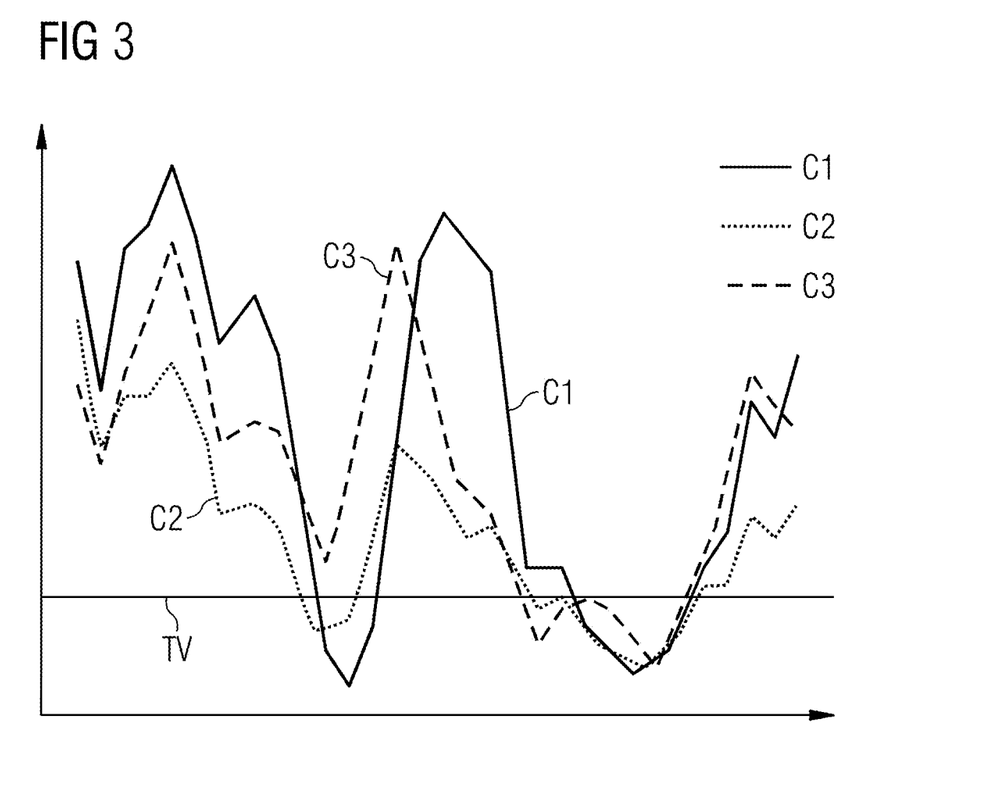
FIG. 3 is a plot of example results of the method according to an exemplary embodiment of the disclosure.

FIG. 3 shows an example of a possible result of the method according to the disclosure regarding a cardiac measurement. Shown is a plot of motion curve for the right coronary artery C1 (solid curve), the motion curve for the left atrium C2 (dashed curve) and the motion curve for the right atrium C3 (dash-dotted curve) generated by the proposed system, as well as a threshold movement value TV for the resting phase detection of the right coronary artery.

The threshold movement value TV, shown as a horizontal line in this figure, is used for detecting resting phases based on the right coronary artery. A value for this threshold can be obtained from some manually annotated example cases, e.g. For the right coronary artery, a threshold of 0.22 mm movement between adjacent images I1, I2, I3 was found based on ROC curve analysis for twenty manually annotated cases.

These regions where a motion curve C1, C2, C3 drops below the threshold movement value TV may later be chosen as suitable resting phases and, therefore, for recording times in the cardiac cycle.

Figure 4:
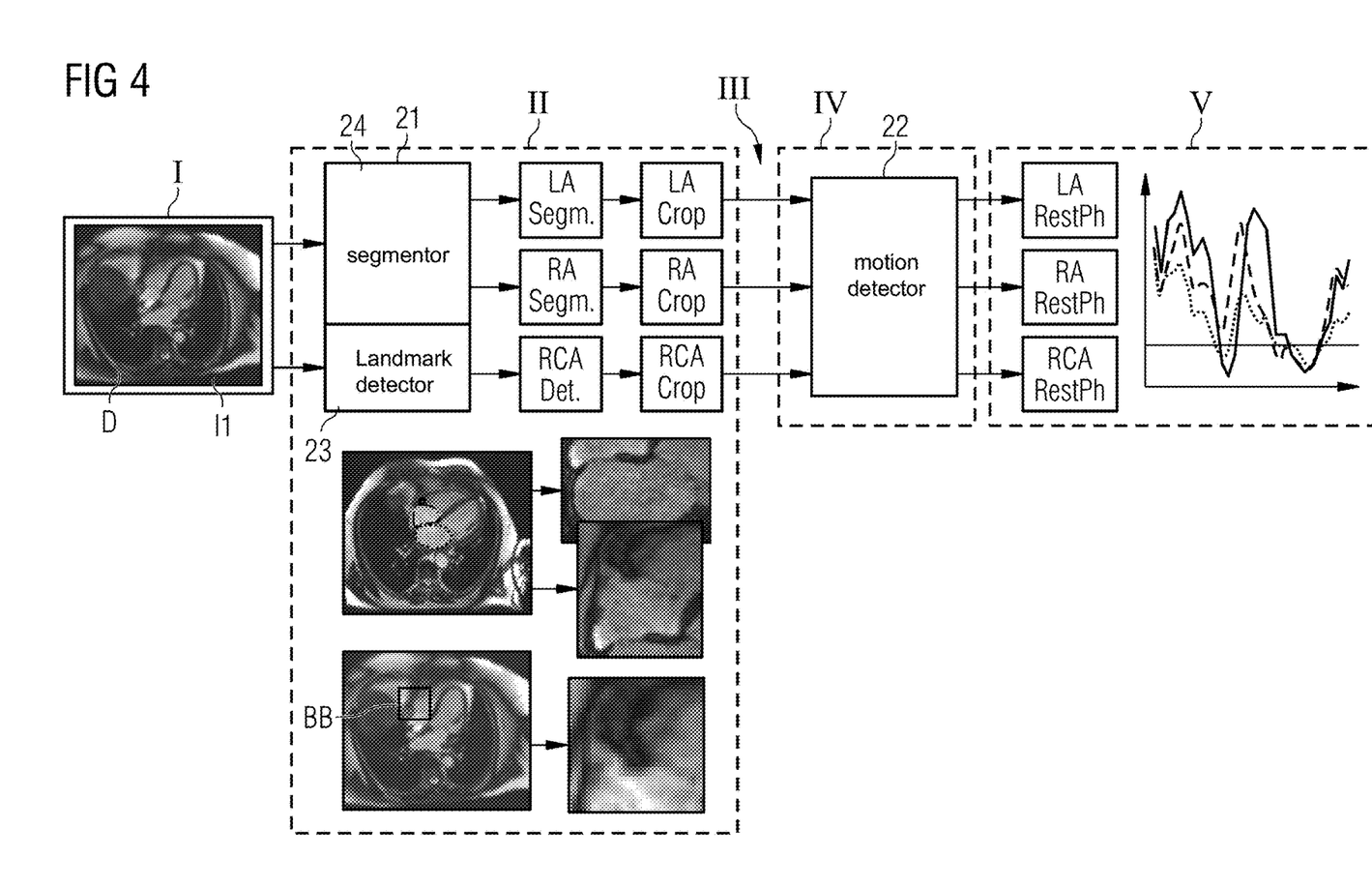
FIG. 4 shows a block diagram of the process flow of a method according to an exemplary embodiment of the disclosure.

FIG. 4 shows a block diagram of the process flow of a preferred example of the method according to the disclosure, especially suitable for static cardiac imaging such as whole-heart coronary imaging.

In step I, a dataset D (e.g. CINE data) of a series of images I1, I2, I3 of a human heart is provided. Here only one image I1 is shown to describe the localization process. The other images I2 I3 would show the same region where the heart would have moved according to its cycle. The aim is to generate the motion curve for the right coronary artery C1, the motion curve for the left atrium C2 and the motion curve for the right atrium C3 motion curves of the shown in FIG. 3. In the following, right coronary artery is abbreviated RCA, left atrium LA and right atrium RA.

In this example, step II (see FIG. 1) comprises a series of subroutines. The dataset (digital images I1, I2, I3) is forwarded to a localizer 21, which comprises a landmark detector 23 and a segmentor 24. Once the dataset is forwarded through the landmark detector 23 and segmentor 24, the localization of the chosen regions of the heart (here RCA, LA, RA) is done. The landmark detector 23 outputs a center point of the ROI (Box "RCA Det.") while the segmentor 24 outputs a contour around the ROI (Boxes "LA Segm." an "RA Segm."). Before sending the data into the motion detector 22, these outputs are used for cropping rectangular areas from the input images containing each ROI (Boxes " . . . Crop"). The pictures in the lower part of the box show a segmented picture (upper left), a picture with a bounding box bb (lower left) and cropped out in respect to bounding boxes BB (right).

In case of the landmark detection, prior knowledge about the size of the anatomy is used to define a bounding box BB centered at the detected landmark position. In case of segmentation, the tightest fitting rectangular bounding box enclosing the contours of all timepoints of the segmented region should be selected. This means that the input image sizes for second network would be variable.

In step III, the calculated localization data LD are sent to the motion detector 22.

In step IV, the movement data of the target T is calculated by the motion detector 22.

In step V, the motion detection is performed while producing the motion curves C1, C2, C3 shown in FIG. 3.

Figure 5:
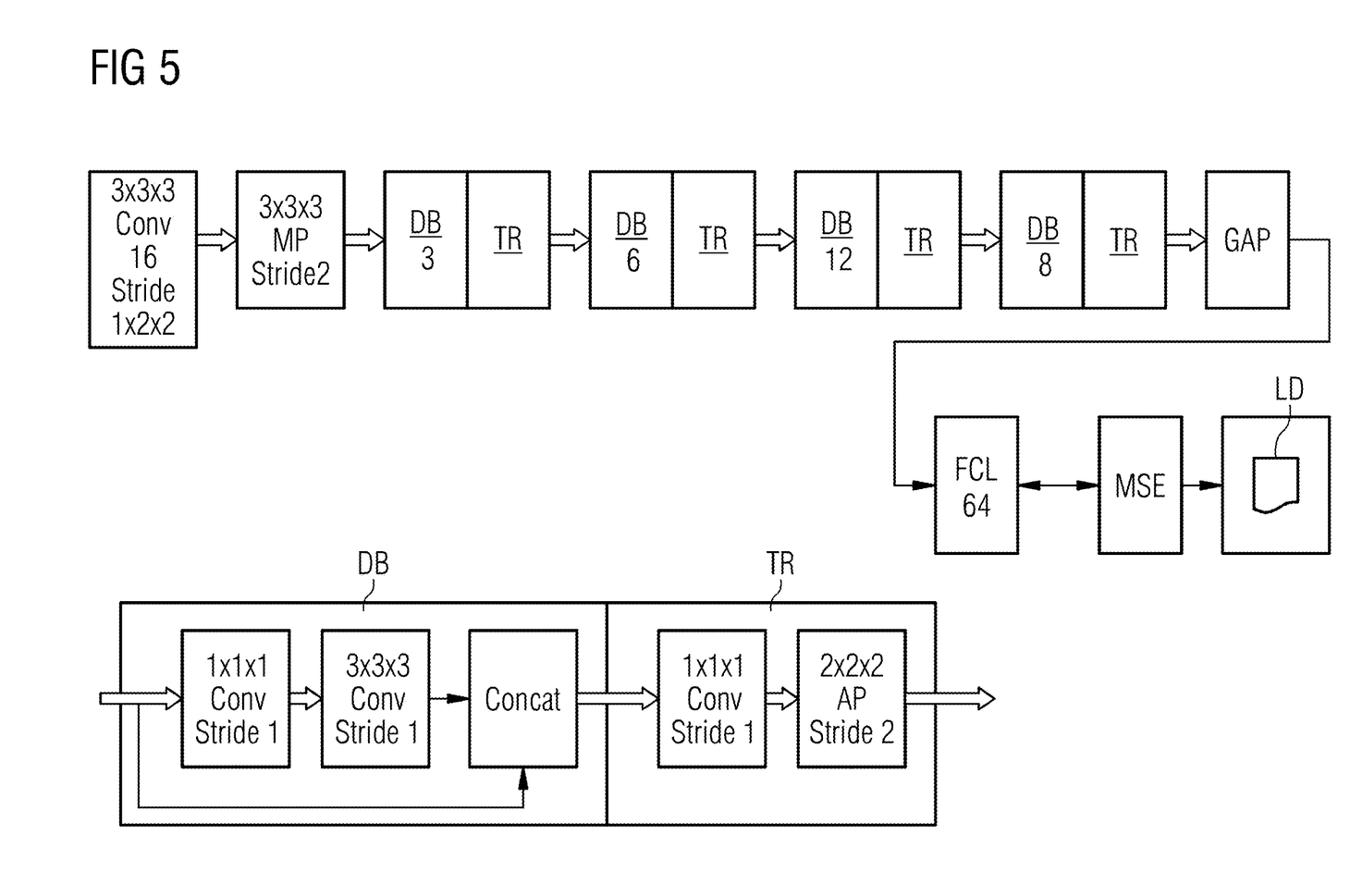
FIG. 5 shows a block diagram of a localizer according to an exemplary embodiment of the disclosure.

Regarding this figure, the landmark detector 23 could be a landmark detection network 23 built with a 3D-DenseNet as shown in FIG. 5. The ground truth used for training the landmark detection network could be the landmark position data. For the segmentor 24, a segmentation network 24 could be used, preferably a state-of-the-art U-net structure. In FIG. 4, the localizer 21 and the motion detector 22 could be formed by chained Deep Neural Networks.

As a preprocessing step, it is preferred that all images were interpolated to a fixed spatial and temporal resolution to be resolution-independent.

FIG. 5 shows a block diagram of a preferred localizer 21 comprising a landmark detection network 23 built with a 3D-DenseNet. In the bottom row, an example of a DenseBlock DB is shown with one dense layer followed by a transition block TR.

The landmark detection network 23 comprises a sequence of discrete blocks with individually defined functionalities. The designations and values shown in these blocks are notations used in the state of the art of 3D-DenseNet networks and are well known by the artisan. It should be noted that outlined arrows represent a 3D batch normalization & ReLU ("rectifier linear unit") of the forwarded data and filled arrows represent a "normal" forwarding of the data.

The network begins with a 3D convolutional layer ("Conv") followed by a 3D max pooling layer ("MP"). Then a series of four DenseBlock DB—Transition block TR combinations follows, where the DenseBlock DB can be repeated multiple times according to the number given in the FIG. 3 times for the first, 6 times for the second, 12 times for the third and 8 times for the fourth). A DenseBlock DB comprises a series of two convolutional layers ("Conv") followed by a concatenation operator ("Concat"), wherein it could be assumed that the grow rate for this exemplary DenseBlock DB is 12 and the bottleneck size ("BN") is 4. The output number of features of the first Conv (1×1×1) in the DenseBlock DB is calculated by multiplying the grow rate and the bottleneck size and the output number of features of the second Conv is controlled by grow rate. With the help of the grow rate and BN, the amount of information each layer contributes to the global state of the network can be controlled. The first Conv in the DenseBlock DB makes the network computationally efficient as this layer can reduce the size of feature maps before forwarding to the next Conv.

A 3×3×3 Conv is used with the setting of zero padding and stride size of 1. It deals with the feature extraction of the input data. For the downsampling at the beginning, a 1×2×2 MP with stride size 2 is followed the first Conv.

The transition block comprises a "Conv"-layer followed by an average pooling layer ("AP"). It is responsible for feature reduction using the 1×1×1 convolutional layer and after each transition layer the number of feature maps is reduced by half, as well as spatial and temporal downsampling using the 2×2×2 AP layer. After the last transition, there follows a global average pooling ("GAP"), a fully connected layer ("FCL") and a layer for the mean square error ("MSE"). The last block represents the localization data LD as the result of the shown network.

Figure 6:
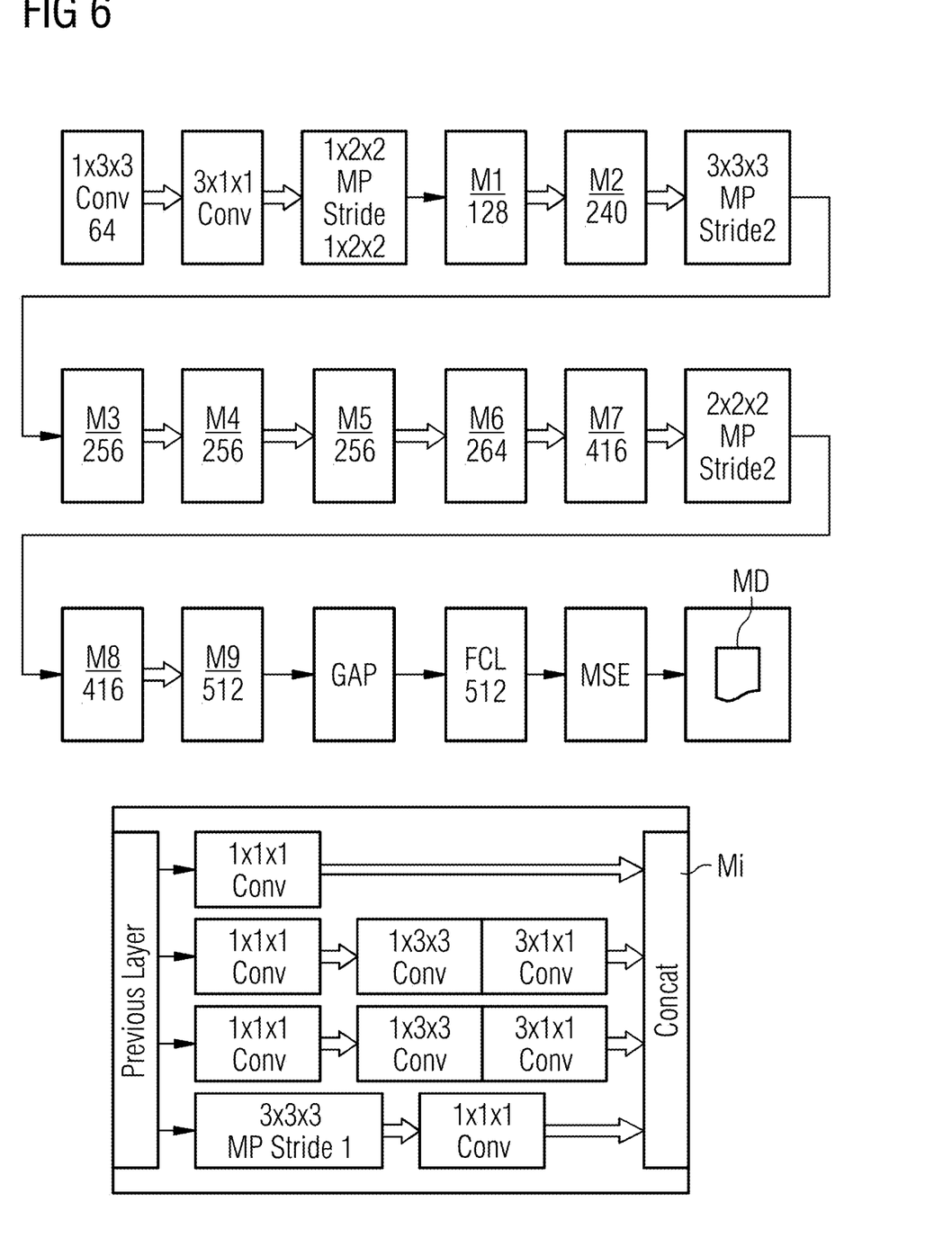
FIG. 6 shows a block diagram of a motion detector according to an exemplary embodiment of the disclosure.

FIG. 6 shows a block diagram of a preferred motion detector 22 in form of a motion detection network 22. After the localization step, the task of this exemplary motion detection network 22 is to generate a quantitative motion curve describing the average motion magnitude between adjacent time frames (images I1, I2, I3) of the cropped CINE series shown in FIG. 4. Ground truth for this motion detection network 22 could be obtained by performing elastic image registration on all images I1, I2, I3 (time frames) of the CINE series and averaging the length of the motion vectors between adjacent images I1, I2, I3. This approach yields a motion curve C1, C2, C3 with an interpretable vertical axis as "average motion in mm per unit of time" and a quiescent phase can be determined from the motion curve C1, C2, C3 by simple thresholding (see e.g. FIG. 3). An example network which was trained for this purpose is based on separable spatio-temporal convolutional layers as shown in this Figure.

The motion detection network 22 comprises a sequence of discrete blocks with individually defined functionalities. The designations and values shown in these blocks are notations used in the state of the art of Spatial Temporal Networks and are well known by the artisan. It should be noted that outlined arrows represent a 3D Instance normalization & ReLU of the forwarded data and filled arrows represent a "normal" forwarding of the data.

The network begins with a series of two convolutional layers ("Conv") followed by a max pooling layer ("MP"). The first convolution operates in the spatial dimensions (1×3×3) and the second in the temporal dimension (3×1×1) to extract spatial and temporal features from the inputs. The downsampling is done by using MP. Then a series of two complex blocks designated with "M" follow. These "M-Blocks" Mi, M1, M2, M3, M4, M5, M6, M7, M8, M9 each comprises four parallel tracks, wherein one track comprises a "Conv"-layer, two tracks comprise a series of three "Conv"-layers and one track comprises a "MP" layer followed by a "Conv"—layer. The 1×1×1 convolution is used for reducing the feature map dimensionality in the M-Blocks. All these four tracks are concatenated by a final "Concat"-block. The two "M-Blocks" M1, M2 follows a "MP"-layer, followed by a series of five "M-Blocks" M3, M4, M5, M6, M7 and an additional "MP"-layer and again two "M-Blocks" M8, M9. After the last "M-Block" M9, there follows a global average pooling ("GAP"), a fully connected layer ("FCL"), a layer for the mean square error ("MSE"). The last block represents the motion data MD as the result of the shown motion detection network 22. The numbers at the bottom of Conv or M-Blocks represent the output number of features.

The motion detection network 22 then outputs a motion curve C1, C2, C3 within a CINE dataset as shown in FIG. 3.

The two networks shown in FIGS. 5 and 6 could be trained and evaluated on 4CHV CINE datasets from a number of patients (e.g. 500-1,000). The full training-dataset could be split into subsets, e.g. a percentage for training, a percentage for validation and a percentage for testing. For RCA detection, the 3D-DenseNet could be validated by calculating the mean and standard deviation of the distance of ground truth and detected landmarks for each time point. For motion detection, the motion detection network 22 could be validated by calculating the root-mean-squared error (RMSE) between the predicted motion curves and the ground truth.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit", "system" or a "device" does not preclude the use of more than one unit, system or device.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for automatic motion detection in medical image-series, comprising:
   providing a dataset of a series of images, the images being of a similar region of interest that are recorded at consecutive points of time;
   localizing, using a localizer that is a first deep neural network, a target in the images of the dataset and calculating a position of the target in the images to calculate localization data of the target; and
   calculating, using a motion detector that is a second deep neural network, movement data of a movement of the target of temporal adjacent images of the images based on the localization data, wherein the first deep neural network of the localizer and the second deep neural network of the motion detector are formed as chained deep neural networks.

2. The method according to claim 1, wherein calculating the localization data comprises performing calculations based on: (a) probabilistic boosting trees and/or random forests or (b) an adaptive algorithm trained for localizing the target in the images of the dataset, and calculating the position of the target in the images.

3. The method according to claim 1, wherein the movement data is calculated based on: (a) image registration of the target in the temporal adjacent images or (b) an adaptive algorithm trained for calculating movement data of the temporal adjacent images based on the localization data, wherein the calculation of the movement data of the target and the calculation of the localization data is performed in a convoluted process with a same adaptive algorithm.

4. The method according to claim 1, wherein calculating the movement data of the movement of the target generates a quantitative motion curve describing an average motion magnitude between the temporal adjacent images, the calculating the movement data including:
   performing an elastic image registration on the series of images combined with averaging lengths of motion vectors between the temporal adjacent images, or
   training an adaptive algorithm with the elastic image registration on the series of images combined with averaging the lengths of motion vectors between the temporal adjacent images.

5. The method according to claim 1, further comprising comparing the calculated movement data of the target with a predefined threshold movement value to perform a motion detection.

6. The method according to claim 5, wherein the threshold movement value is obtained from one or more predefined annotated example cases, selected based on physiological knowledge, and/or selected based on a predefined image resolution.

7. The method according to claim 1, wherein, before calculating the movement data, the localization data is used for cropping areas as a bounding box from the images containing the target, wherein, in case of segmentation, a tightest fitting bounding box enclosing contours of all time-points of the target is selected.

8. The method according to claim 1, wherein the method provides an automatic motion detection in CINE data, the target in the images including image data of coronary arteries, right or left atrium, and/or right or left ventricle.

9. A system for automatic motion detection in medical image-series, the system comprising:
    a data interface configured to receive a dataset of a series of images of a similar region of interest that are recorded at consecutive points of time;
    a localizer that is a first deep neural network and configured to localize a target in the images of the dataset to calculate localization data of the target, and calculate a position of the target in the images; and
    a motion detector that is a second deep neural network and configured to calculate movement data of a movement of the target of temporal adjacent images of the images based on the localization data, wherein the first deep neural network of the and the second deep neural network of the motion detector are formed as chained deep neural networks.

10. The system according to claim 9, wherein the localizer comprises:
    a landmark detector configured to obtain landmark position data and/or a center point based on a position of the target; and/or
    a segmentor configured to obtain contours around the target or a segmented region.

11. The system according to claim 10, wherein the landmark detector comprises a 3D-DenseNet, and the segmentor comprises a U-net structure.

12. The system according to claim 9, wherein the localizer comprises:
    a landmark detector configured to obtain landmark position data and/or a center point based on a position of the target; and
    a segmentor configured to obtain contours around the target or a segmented region.

13. The system according to claim 9, wherein the localizer and/or the motion detector comprise a trained machine learning network.

14. The system according to claim 13, wherein the trained machine learning network comprises a neural network, a convolutional network, and/or an end-to-end network.

15. The system according to claim 9, wherein the localizer and the motion detector are part of a data-network in data-communication with a magnetic resonance imaging system, wherein the data network includes parts of the internet and/or a cloud-based computing system.

16. A controller configured to control a medical imaging system comprising the system according to claim 9.

17. A medical imaging system comprising:
    a medical image scanner; and
    a controller comprising a localizer that is a first deep neural network and a motion detector that is a second deep network, the controller being configured to:
        generate a dataset of a series of images, the images being of a similar region of interest that are recorded at consecutive points of time;
        localize, using the first deep neural network of the localizer, a target in the images of the dataset and calculating a position of the target in the images to calculate localization data of the target; and
        calculate, using the second deep neural network of the motion detector, movement data of a movement of the target of temporal adjacent images of the images based on the localization data, wherein the first deep neural network of the localizer and the second deep neural network of the motion detector are formed as chained deep neural networks.

18. A non-transitory computer program product having a computer program which is directly loadable into a memory of a medical imaging system, when executed a controller of the system, causes the system to perform the method as claimed in claim 1.

19. A non-transitory computer-readable storage medium with an executable program stored thereon, that when executed, instructs a processor to perform the method of claim 1.

20. The method according to claim 1, wherein the output of the first deep neural network is provided as an input to the second deep neural network to form the chained deep neural networks.

* * * * *